United States Patent

Eggler

[11] Patent Number: 5,280,039
[45] Date of Patent: Jan. 18, 1994

[54] BICYCLIC CARBAMATES AND METHODS OF TREATING INFLAMMATORY DISEASES USING THE SAME

[75] Inventor: James F. Eggler, Stonington, Conn.

[73] Assignee: Pfizer Inc., New York, N.Y.

[21] Appl. No.: 971,781

[22] Filed: Nov. 4, 1992

[51] Int. Cl.$^5$ .................. A61K 31/405; C07D 209/08; C07D 405/12

[52] U.S. Cl. ..................... 514/414; 514/415; 548/454; 548/510

[58] Field of Search ............. 548/454, 510; 514/414, 514/415

[56] References Cited

U.S. PATENT DOCUMENTS 4,661,596  4/1987  Kreft et al. ................... 546/152
5,059,609  10/1991  Eggler et al. .................. 514/314

Primary Examiner—Robert W. Ramsuer
Assistant Examiner—Jacqueline Haley
Attorney, Agent, or Firm—Peter C. Richardson; Paul H. Ginsburg; Gezina Holtrust

[57] ABSTRACT

A compound of the formula

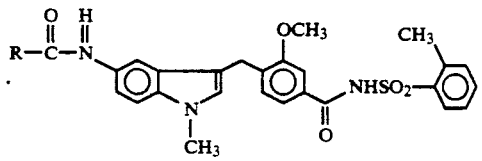

wherein R is defined herein is useful as an anti-inflammatory agent.

6 Claims, No Drawings

BICYCLIC CARBAMATES AND METHODS OF TREATING INFLAMMATORY DISEASES USING THE SAME

BACKGROUND OF THE INVENTION

This invention relates to novel bicyclic carbamate compounds, pharmaceutical compositions comprising such compounds and the use of such compounds as therapeutic agents. The compounds block leukotriene receptors and are useful as anti-inflammatory agents.

It is known that arachidonic acid (AA) is metabolized in mammals by two distinct pathways. The metabolism of arachidonic acid by cyclooxygenase enzymes results in the production of prostaglandins and thromboxanes. The other pathway of AA metabolism involves lipoxygenase enzymes and results in the production of a number of oxidative products called leukotrienes. The latter are designated by the LT nomenclature system, and one of the most significant products of the lipoxygenase metabolic pathway is the leukotriene $D_4$. Leukotrienes participate in inflammatory reactions, exhibit chemotactic activities, stimulate lysosomal enzyme release and act as important factors in the immediate hypersensitivity reaction. For example, LTD4 is a potent bronchoconstrictor of the human bronchi.

The biological activity of the leukotrienes and of 5-lipoxygenase as the enzyme leading to the metabolism of AA to leukotrienes, indicates that a rational approach to drug therapy to prevent, remove or ameliorate the symptoms of anaphylaxis, asthma and inflammation must focus on either blocking the release of mediators of these conditions or antagonizing their effects. Thus, compounds which inhibit the biological effects of the leukotrienes and/or which control the biosynthesis of these substances, as by inhibiting 5-lipoxygenase, are considered to be of value in treating such conditions as allergic bronchial asthma as well as in other immediate inflammatory reactions.

Eggler et al., in PCT Patent Application PCT/US87/02745, describe racemic or optically active substituted tetralins, chromans and related compounds that inhibit 5-lipoxygenase enzyme and antagonize LTB4 and LTD4, and are therefore useful in the prevention and treatment of asthma, arthritis, psoriasis, ulcers, and myocardial infarction. Kreft et al., in U.S. Pat. No. 4,661,596, describe disubstituted naphthalenes, dihydronaphthalenes and tetralins that inhibit lipoxygenase enzyme and antagonize LTD4, and are therefore useful in the prevention and treatment of asthma.

SUMMARY OF THE INVENTION

The present invention relates to a compound of the formula

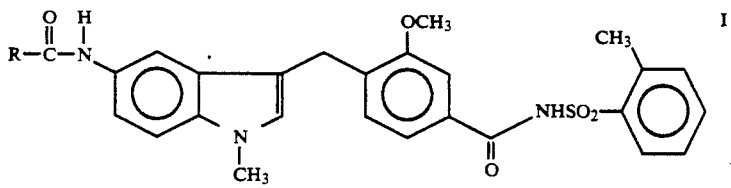

wherein R is exo-norborneyloxy, endo-norborneyloxy, exo-norbornyloxy, endo-norbornyloxy, isopinocamphyloxy, myrtanyloxy, mytenloxy, 1-adamantanyloxy, 2-adamantanyloxy, fenchanyloxy, isobornyloxy, verbenyloxy, endo-7-oxabicyclo[2.2.1]heptanyloxy, exo-7-oxabicyclo[2.2.1]heptanyloxy, 5-norbornene-2-methyloxy, 2-norbornanemethyloxy or 7-bicyclo[2.2.1]heptanyloxy.

The present invention also relates to a pharmaceutical composition for the treatment or prevention of asthma, anaphylaxis, and/or other inflammatory diseases comprising an amount of a compound of formula I effective in treating or preventing one of said diseases, e.g., allergic lung disorders, allergic skin diseases, ectopic and atopic eczemas, psoriasis, contact hypersensitivity, angioneurotic oedema, bronchitis, cystic fibrosis, rheumatic fever, vascular diseases, inflammatory bowel disease and allergic diseases of the eye.

The present invention also relates to a method for the treatment or prevention of asthma and/or other inflammatory diseases comprising administering to a mammal in need of said treatment or prevention a compound of formula I in an amount effective to treat or prevent any one of said diseases.

The present invention also relates to a method of inhibiting 5-lipoxygenase enzyme in a mammal, comprising administering to a mammal an amount of a compound of formula I effective in inhibiting 5-lipoxygenase enzyme.

The present invention also relates to a method of blocking receptors of leukotriene D4 in a mammal comprising administering to a mammal an amount of a compound of formula I effective in blocking receptors of said leukotriene.

DETAILED DESCRIPTION OF THE INVENTION

The following reaction scheme illustrates the preparation of the compounds of the present invention.

Scheme 1

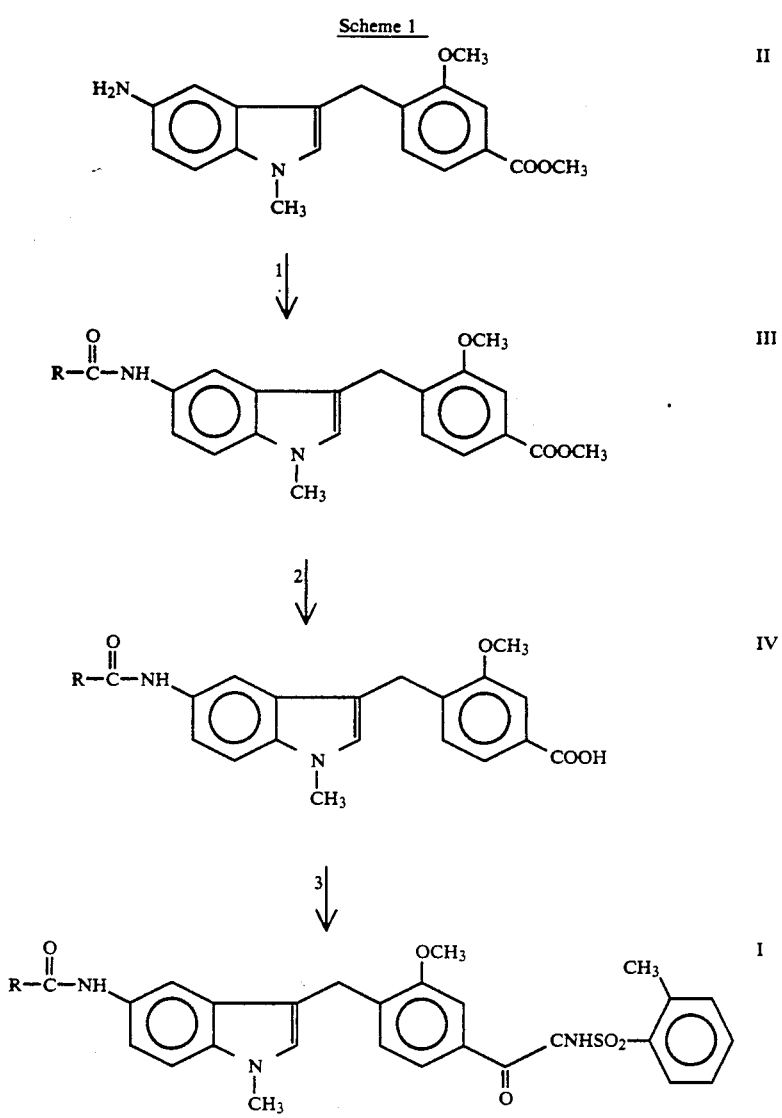

The compound of formula II, the starting material used in Scheme 1, may be prepared as described in European Patent Application 199,543.

In reaction 1 of Scheme 1, the compound of formula II is converted to the methyl 4-[5-(bicyclicoxycarbonyl)amino-1-methylindol-3-ylmethyl]-3-methoxybenzoate compound of formula III by reacting II with a bicyclic chloroformate of the formula $$RC(=O)-Cl$$

wherein R is as defined with reference to formula I and N-methylmorpholine in a polar aprotic solvent. The preferred polar aprotic solvent is dichloromethane. The reaction is stirred, at room temperature, overnight for convenience.

In reaction 2 of Scheme 1, the compound of formula III is converted to the 4-[5-(bicyclicoxycarbonyl)amino-1-methylindol-3-ylmethyl]-3-methoxybenzoic acid compound of formula IV by reacting III with aqueous lithium hydroxide in a methanol/tetrahydrofuran solution. The reaction was stirred at room temperature for a time period between about 15 hours to about 25 hours, preferably about 20 hours.

In reaction 3 of Scheme 1, the compound of formula IV is converted to the N-[4-[5-(bicycliocoxycarbonyl)amino-1-methylindol-3-ylmethyl]-3-methoxybenzoyl]-2-methylbenzenesulfonamide compound of formula I by adding a solution of a carbodiimide such as dicyclohexylcarbodiimide or 1-(3-dimethylaminopropyl)-3-ethylcarbodiimide, preferably 1-(3-dimethylaminopropyl)-3-ethylcarbodiimide, in a polar aprotic solvent such as chloroform, tetrahydrofuran or dichloromethane, preferably dichloromethane, to a solution of an organic base such as pyridine or 4-(dimethylamino)pyridine, preferably 4-(dimethylamino)pyridine, and a sulfonamide preferably 2-methylbenzene sulfonamide in a polar aprotic solvent, preferably dichloromethane. The resulting reaction mixture is stirred for a time period between about 15 hours to about 25 hours, preferably about 20 hours, at a temperature between about 0° C. to about room temperature, preferably room temperature.

The novel compounds of formula I are useful as inhibitors of 5-lipoxygenase enzyme and antagonists of leukotriene D4.

The in vitro activity of the compounds of formula I may be tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed 1 time with RPMI 1640 (GIBCO) and resuspended in RPMI 1640 plus 1 microM glutathione to a cell density of $1 \times 10$ cells/ml. A volume of 0.5 ml of the cell suspension is incubated at 30° C. with 0.001 m of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minutes incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent systems of acetonitrile/H$_2$O/acetic acid (9.1%) with a linear acetonitrile gradient from 35% to 70% over 15 minutes at 1 ml/minute. Quantitation is accomplished with a Berthold Radioactivity Monitor equipped with a build-in integrator and a 0.2 ml flow cell mixing 2.4 ml/minute Omnifluor (NEN) with column effluent. Integration units for each product are calculated as a percentage of total integration units, and then compared to the average control levels. The results are expressed as "Percent of Control" and are plotted vs the log of drug concentration. The IC$_5$ values are estimated by graphical inspection.

The ability of the compounds of formula I to compete with radiolabelled LTD4 for specific receptor cites on guinea pig lung membranes may be tested as described by Cheng et al, Biochemical and Biophysical Research Communication, 118, 1, 20–26 (1984).

To evaluate the compounds of the formula I in vivo, they are tested by the socalled PAF lethality assay procedure:

Materials:
Mice: DC1 males, all approximately the same weight (approximately 26 grams), 12 per group.
Vehicle for oral drug dosing: EES (5% ethanol, 5% emulphor, 90% saline). Stored at room temperature.
Drugs: For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.
Vehicle for i.v. Injection: Saline with 2.5 mg/ml Bovine Serum Albumin (BSA, Sigma #A4378) and 0.05 mg/ml Propranolol (Sigma #P0884). Prepared fresh daily and kept at room temperature.
Platelet Activating Factor (PAF): A 10 microM stock solution is prepared by dissolving mg PAF (Calbiochem #429460) in 0.18 ml ethanol. This is stored at $-20°$ C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control: Phenidone is used at 25 mg/kg (its approximate ED 50).

Method:
45 minutes before PAF injection, mice are treated orally with drug using 0.1 ml/10 grams body weight. 35 to 40 minutes they are placed under a heat lamp to dilate the caudal vein for PAF injection. PAF is injected i.v. at 0.1 mg/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided.

Variations:
1. The time for oral dosing can be changed.
2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

For use in the prevention or treatment of asthma, anaphylaxis and inflammation in a mammal, including man, a compound of the formula I is given in an amount effective to treat any one of such diseases, and of about 0.5 to about 50 mg/kg/day, in single or divided daily doses. A more preferred dosage range is about 2 to about 20 mg/kg/day, although in particular cases, at the discretion of the attending physician, doses outside the broader range may be required. The preferred route of administration is generally oral, but parenteral administration, e.g., intramuscular, intravenous, intradermal, will be preferred in special cases, e.g., where oral absorption is impaired as by disease, or the patient is unable to swallow. The compounds of formula I can also be administered topically, e.g. to treat psoriasis, or in an aerosol, e.g. to treat asthma.

The compounds of the present invention are generally administered in the form of pharmaceutical compositions comprising at least one of the compounds of the formula I, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like; for topical administration, in the form of a gel, lotion or cream; and for administration by inhalation, in the form of an aerosol spray given in an amount of about 100 to about 1000 μg/dose, effective to treat any one of said diseases.

EXAMPLE 1

A. Methyl 3-methoxy-4-methylbenzoate

A solution of 3-methoxy-4-methylbenzoic acid (10 grams) in 200 mL of methanol was saturated with hydrochloric acid gas. The resulting solution was warmed on a steam bath for 4 hours. The reaction was allowed to cool and the methanol was evaporated. The residue was dissolved in ethyl acetate and the ethyl acetate layer was washed with water, dried over sodium sulfate and evaporated to give the title compound. NMR (CDCl$_3$) δ:2.15 (s, 3H), 3.80 (s, 3H), 7.48–7.18 (m, 3H).

B. Methyl 3-methoxy-4-bromomethylbenzoate

A solution of methyl 3-methoxy-4-methylbenzoate (10 grams) and 2,2-azobis(2-methyl-propionitrile) (25 milligrams) in carbon tetrachloride (200 mL) was heated to gentle reflux. Bromine (9 grams) was added in portions and resulting solution was heated at reflux for 1 hour then stirred at room temperature overnight. The carbon tetrachloride was evaporated and the residue dissolved in ether. The ether solution was washed with water. The ether layer was dried over sodium sulfate then evaporated to give 13.9 grams of crude product. NMR (CDCl$_3$) δ:3.92 (s, 3H), 4.45 (s, 2H), 7.65–7.00 (m, 3H).

C. Methyl 3-methoxy-4-(5-nitroindol-3-ylmethyl)benzoate

Silver oxide (2.32 grams) was added to a solution of 5-nitroindole (1.62 grams) and methyl 4-bromoethyl-3-methoxybenzoate (2.6 grams) in 10 mL of dioxane. The mixture was heated at 60° for 20 hours. The dioxane was evaporated and ethyl acetate was added to the residue. The resulting suspension was filtered. The filtrate was evaporated and the residue was purified on silica with hexane/ethyl acetate to give 1.8 grams of title compound, m.p. 162°–163°.

D. Methyl 3-methoxy-4-(1-methyl-5-nitroindol-3-ylmethyl)benzoate

Sodium hydride (212 milligrams) was added to a solution of methyl 3-methoxy-4-(5-nitroindol-3-ylmethyl)benzoate (1.8 grams) in 60 mL of dry tetrahydrofuran. After stirring for 10 minutes, methyl iodide (753 milligrams) was added and the reaction was stirred at room temperature for 2 hours. The volatiles were evaporated and the residue dissolved in ethyl acetate. The ethyl acetate layer was washed with water, dried over sodium sulfate and evaporated. The residue was purified on silica gel with dichloromethane to give 1.8 grams product, m.p. 151°–153°.

E. Methyl 4-(5-amino-1-methylindol-3-ylmethyl)-3-methoxybenzoate

A solution of methyl 3-methoxy-4-(1-methyl-5-nitroindol-3-ylmethyl)benzoate (1.5 grams) in 50 mL of tetrahydrofuran was hydrogenated at 40 p.s.i. in the presence of 10% palladium-on-carbon (0.3 grams) for 3 hours. The reaction was filtered and the filtrate evaporated to give 1.5 grams of title compound. NMR (CDCl$_3$) δ:3.35, (broad s, 2H), 3.65 (s, 3H), 3.95 (s, 3H), 4.05 (s, 2H), 6.85 (m, 3H), 7.10 (m, 2H), 7.50 (m, 2H).

F. Exo-2-norbornyl chloroformate

A solution of exo-norborneol (10 grams) in 125 mL of toluene was cooled to 0°. A 1.93M solution of phosgene in toluene (56 mL) was added dropwise. The reaction was allowed to warm to room temperature and stirred overnight. The volatiles were evaporated and title compound (8.9 grams) was either used without further purification or isolated by distillation. NMR (CDCl$_3$) δ:1.90–1.00 (m, 8H), 2.30 (broad s, 1H), 2.45 (broad s, 1H), 4.25 (d, 1H).

G. Methyl 4-[5-(exo-2-norbornyloxycarbonyl)amino-1-methylindol-3-ylmethyl]-3-methoxybenzoate A solution of methyl 4-(5-amino-1-methylindol-3-ylmethyl)-3-methoxybenzoate (500 grams), exo-2-norbornyl chloroformate (297 mgrams) and N-methylmorpholine (465 milligrams) in 35 mL of dichloromethane was stirred at room temperature overnight. The dichloromethane layer was washed with 1N HCl and water then dried over sodium sulfate. Evaporation of the volatiles gave the title compound (660 milligrams) as a foam. NMR (CDCl$_3$) δ:1.75–1.00 (m, 5H), 2.30 (m, 4H), 3.75 (s, 3H), 3.85 (s, 3H), 3.95 (s, 3H), 4.60 (d, 1H), 6.50 (broad s, 1H), 7.60–6.70 (m, 7H).

H. 4-[5-(exo-2-norbornyloxycarbonyl)amino-1-methylindol-3-ylmethyl]-3-methoxybenzoic acid A solution of lithium hydroxide (275 milligrams) in 3 mL of water was added to a solution of methyl 4-[5-(exo-2-norbornyloxycarbonyl)amino-1-methylindol-3-ylmethyl]-3-methoxybenzoate (660 milligrams) in 10 mL of methanol and 10 mL of tetrahydrofuran. The reaction was stirred at room temperature for 20 hours and then concentrated. The resulting solution was acidified 1M HCl and extracted with ethyl acetate. The ethyl acetate layer was dried and evaporated to 700 milligrams of crude product which was purified by chromatography on silica gel with dichloromethane/methanol to give the title compound (470 milligrams). NMR (CDCl$_3$) δ:1.80–1.00 (m, 8H), 2.40 (m, 2H), 3.70 (s, 3H), 3.90 (s, 3H), 4.10 (s, 2H), 7.60–6.50 (m, 9H).

I. N-[4-[5-(exo-2-norbornyloxy carbonyl)amino-1-methylindol-3-ylmethyl]-3-methoxybenzoyl]-2-methyl benzenesulfonamide A solution of 1-(3-dimethylaminopropyl)-3-ethylcarbodiimide (239 milligrams) in 3 mL of dichloromethane was added to a solution of 4-[5-(exo-2-norbornyloxycarbonyl)amino-1-methylindol-3-ylmethyl]-3-methoxy benzoic acid (370 milligrams), 4-(dimethylamino)pyridine (153 milligrams) and 2-methyl benzene sulfonamide (214 milligrams) in 35 mL of dichloromethane. The mixture was stirred for 20 hours then washed with water and 1N HCl. The dichloromethane layer was dried over sodium sulfate and evaporated. The crude product was purified by chromatography on silica gel with dichloromethane/methanol to give the title compound (297 milligrams) as a foam. Mass Spec. p+601.2, Base 94.1, NMR (CDCl$_3$) δ:1.6–0.9 (m, 8H), 2.1 (m, 2H), 2.45 (s, 3H), 3.50 (s, 3H), 3.65 (s, 3H), 3.85 (s, 2H), 4.40 (d, 1H), 7.30–6.30 (m. 11H), 8.10 (d, 1H).

EXAMPLE 2

A. Endo-2-norbornyl chloroformate

Using a similar procedure to that described in Example 1F, from endonorborneol (5 grams) and phosgene in toluene (25 mL) there was obtained 4.8 grams of title compound which was used without further purification. NMR (CDCl$_3$) δ:2.10–1.10 (m, 8H), 2.30 (broad s, 1H), 2.60 (broad s, 1H), 5.10 (m, 1H).

B. Methyl 4-[5-(endo-2-norbornyloxycarbonyl)amino-1-methylindol-3-ylmethyl]-3-methoxybenzoate Using a similar procedure to that described in Example 1G, from methyl 4-[5-amino-1-methylindol-3-ylmethyl]-3-methoxybenzoate (500 milligrams), endo-2-norbornyl chloroformate (297 milligrams) and n-methylmorpholine (465 milligrams), there was obtained 760 milligrams of title compound as a foam. NMR (CDCl$_3$) δ:2.10–1.00 (m, 8H), 2.25 (broad s, 1H), 2.50 (broad s, 1H), 3.70 (s, 3H), 3.85 (s, 3H), 3.95 (s, 3H), 4.05 (s, 2H), 5.05 (m, 1H), 6.55 (broad s, 1H), 7.60–6.70 (m, 7H).

C. N-[4-[5-(endo-2-norbornyloxy carbonyl)amino-1-methylindol-3-ylmethyl]-3-methoxybenzoyl]-2-methyl benzene sulfonamide Using a similar procedure to that described in Example 1I, from 4-[5-(endo-2-norbornylcarbonyl)amino-1-methylindol-3-ylmethyl]-3-methoxybenzoic acid (490 milligrams), 4-(dimethylamino)pyridine (201 milligrams), 1-(3-dimethylaminopropyl)-3-ethylcarbodiimide (315 milligrams) and 2-methyl benzene sulfonamide (282 milligrams), there was obtained 360 milligrams of title compound as a foam. Mass Spec. p+601.2, Base 161.1, NMR (CDCl$_3$) δ:2.1–1.0 (m, 8H), 2.20 (broad s, 1H), 2.50 (broad s, 1H), 2.15 (s, 3H), 3.70 (s, 3H), 3.85 (s, 3H), 4.00 (s, 2H), 5.00 (m, 1H), 7.50–6.60 (m, 11H), 8.25 (d, 1H), 9.05 (broad s, 1H).

I claim:

1. A compound of the formula

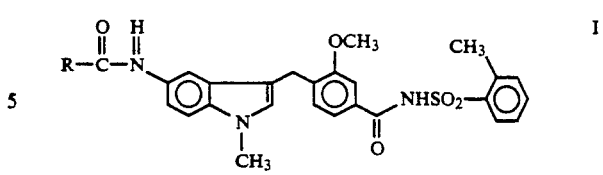

wherein R is exo-bicyclo[2.2.1]hept-5-en-2-oxy, endobicyclo[2.2.1]hept-5-en-2-oxy, exo-bicyclo[2.2.1]heptan-2-oxy, endo-bicyclo[2.2.1]heptan-2-oxy, 2,6,6-trimethylbicyclo[3.1.1]heptan-3-oxy, [6,6-dimethyl-bicyclo[3.1.1]hept-2-yl]methoxy, (6,6-dimethyl-bicyclo[3.1.1]hept-2-en-2-yl)methoxy, adamantan-1-oxy, adamantan-2-oxy, 1,3,3-trimethylbicyclo[2.2.1]heptan-2-oxy, endo-1,7,7-trimethylbicyclo[2.2.1]heptan-2-oxy, 4,6,6-trimethylbicyclo[3.1.1]hept-3-en-2oxy, endo-7-oxabicyclo[2.2.1]heptan-2-oxy, exo-7-oxabicyclo[2.2.1]heptan-2-oxy, bicyclo[2.2.1]hept-5-en-2-oxy, (bicyclo[2.2.1]heptan-2-yl)methoxy or bicyclo[2.2.1]heptan-7-oxy.

2. A compound according to claim 1, wherein R is exobicyclo[2.2.1]heptan-2-oxy or endo-bicyclic[2.2.1]heptan-2-oxy.

3. A pharmaceutical composition for the treatment of asthma, anaphylaxis or other inflammatory diseases comprising an amount of a compound according to claim 1 effective in treating one of said diseases.

4. A method for the treatment of asthma or other inflammatory diseases comprising administering to a mammal in need of said treatment a compound according to claim 1 in an amount effective to treat one of said diseases.

5. A method of inhibiting 5-lipoxygenase enzyme in a mammal, comprising administering to a mammal an amount of a compound according to claim 1 effective in inhibiting 5-lipoxygenase enzyme.

6. A method of blocking receptors of leukotriene D4 in a mammal comprising administering to a mammal an amount of a compound according to claim 1 effective in blocking receptors of said leukotriene.

* * * * *